(12) United States Patent
Chander et al.

(10) Patent No.: US 10,791,072 B2
(45) Date of Patent: Sep. 29, 2020

(54) GENERATING CONVERSATIONS FOR BEHAVIOR ENCOURAGEMENT

(71) Applicant: FUJITSU LIMITED, Kawasaki-shi, Kanagawa (JP)

(72) Inventors: Ajay Chander, San Francisco, CA (US); Sanam Mirzazad Barijough, Mountain View, CA (US)

(73) Assignee: FUJITSU LIMITED, Kawasaki (JP)

( * ) Notice: Subject to any disclaimer, the term of this patent is extended or adjusted under 35 U.S.C. 154(b) by 670 days.

(21) Appl. No.: 14/853,787

(22) Filed: Sep. 14, 2015

(65) Prior Publication Data
US 2017/0078224 A1    Mar. 16, 2017

(51) Int. Cl.
| H04L 12/58 | (2006.01) |
| A61B 5/024 | (2006.01) |
| G06Q 50/00 | (2012.01) |
| A61B 5/00 | (2006.01) |
| A61B 5/01 | (2006.01) |
| A61B 5/021 | (2006.01) |
| A61B 5/11 | (2006.01) |

(52) U.S. Cl.
CPC ........ H04L 51/046 (2013.01); A61B 5/02438 (2013.01); G06Q 50/01 (2013.01); A61B 5/0002 (2013.01); A61B 5/01 (2013.01); A61B 5/021 (2013.01); A61B 5/11 (2013.01); A61B 5/4806 (2013.01)

(58) Field of Classification Search
CPC ...................................................... G06Q 50/01
USPC ........................................................ 434/236
See application file for complete search history.

(56) References Cited

U.S. PATENT DOCUMENTS

| 2003/0028498 A1 | 2/2003 | Hayes-Roth | |
| 2009/0205552 A1 | 8/2009 | Urbanek | |
| 2012/0190446 A1* | 7/2012 | Rogers | G06Q 10/00 463/31 |
| 2014/0099614 A1* | 4/2014 | Hu | G09B 19/00 434/236 |
| 2014/0272849 A1* | 9/2014 | Bhatia | G09B 19/00 434/237 |

FOREIGN PATENT DOCUMENTS

| JP | 2004-227522 A | 8/2004 |
| JP | 2009-205552 A | 9/2009 |

(Continued)

OTHER PUBLICATIONS

"Establishing and maintaining long-term human-computer relationships" Bickmore et al., ACM Transactions on Computer-Human Interaction, vol. 12, No. 2, Jun. 2005.

(Continued)

*Primary Examiner* — Thomas J Hong
(74) *Attorney, Agent, or Firm* — Maschoff Brennan

(57) ABSTRACT

A method may include receiving a goal of a user. The method may also include obtaining progress data related to accomplishment of the goal by the user from a sensor. The method may further include determining, based on the progress data, a progress level of the first user. The progress level may correspond to progress of the first user with respect to accomplishment of the goal. Moreover, the method may include generating a conversation with the user by a virtual agent based on the progress level.

12 Claims, 9 Drawing Sheets

(56) References Cited

FOREIGN PATENT DOCUMENTS

| JP | 2009-238251 A | 10/2009 |
|----|---------------|---------|
| JP | 2014-529144 A | 10/2014 |

OTHER PUBLICATIONS

"Is Having Babies Contagious? Estimating Fertility Peer Effects Between Siblings" Ilyana Kuziemko, Jun. 2006.
"Peer Effects with Random Assignment: Results for Dartmouth" Bruce Sacerdote, National Bureau of Economic Research, Jan. 2000.
"Virtual peers as partners in storytelling and literacy learning" K. Ryokai et al., Journal of Computer Assisted Learning, 2003.
"Preparing Students for Future Learning with Teachable Agents" Doris B. Chin, et al., Educational Technology Research and Development, Dec. 1, 2010.
"Narrative Planning: Balancing Plot and Character" Mark O. Riedl and R. Michael Young, Journal of Artificial Intelligence Research 39, 2010.
"Creating a Story-Telling Universe" Michael Lobowitz, Columbia University, Department of Computer Science, 1983.
"A 'Companion' ECA with Planning and Activity Modeling" Marc Cavazza et al., 2008.
JP Office Action in Application No. 2016-178701 dated Aug. 11, 2020.

* cited by examiner

GENERATING CONVERSATIONS FOR BEHAVIOR ENCOURAGEMENT

FIELD

The embodiments discussed in the present disclosure are related to generating conversations for behavior encouragement.

BACKGROUND

Unless otherwise indicated, the materials described in the background section are not prior art to the claims in the present disclosure and are not admitted to be prior art by inclusion in this section. Technology may be designed to encourage attitudes or behaviors of users through, for example, persuasion or social influence. While technology may be designed to help users create good habits, behavior change is difficult and many attempts fail.

The subject matter claimed in the present disclosure is not limited to embodiments that solve any disadvantages or that operate only in environments such as those described above. Rather, this background is only provided to illustrate one example technology area where some embodiments described may be practiced.

SUMMARY

According to an aspect of an embodiment, a method may include receiving a goal of a user. The method may also include obtaining data related to accomplishment of the goal by the user from a sensor. The method may further include determining, based on the progress data, a progress level of the first user. The progress level may correspond to progress of the first user with respect to accomplishment of the goal. Moreover, the method may generating a conversation with the user by a virtual agent based on the progress level.

The object and advantages of the present disclosure will be realized and achieved at least by the elements, features, and combinations particularly pointed out in the claims.

It is to be understood that both the foregoing general description and the following detailed description are given as examples and are explanatory and are not restrictive of the invention, as claimed.

BRIEF DESCRIPTION OF THE DRAWINGS

Example embodiments will be described and explained with additional specificity and detail through the use of the accompanying drawings in which.

DESCRIPTION OF EMBODIMENTS

Figure 1A:
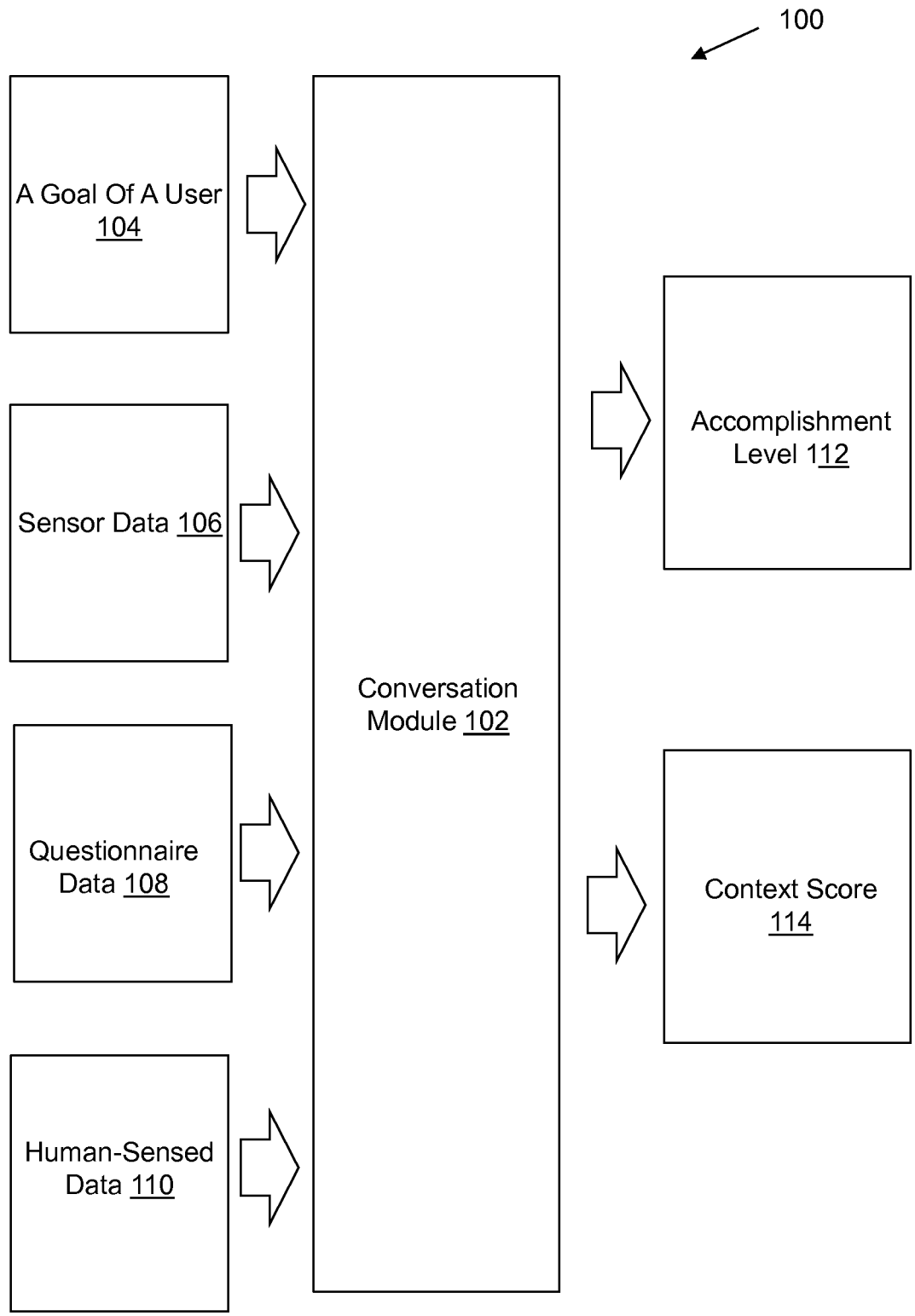
FIG. 1A is a diagram representing an example system configured to determine a quantity of a goal that has been accomplished by a user and/or a context score.

A story may encourage behavior of a listener, particularly when the story is related to a goal of the listener. The listener may contemplate performing a similar action as conveyed by the story in order to accomplish the goal. Thus, the story may help the listener accomplish his or her goal. The term "action," as referred to in the present disclosure, may correspond to a story related to a goal of a user. Some embodiments described in the present disclosure may relate to generating conversations that include stories related to the goal of the user for behavior encouragement. In particular, in some embodiments, content corresponding to an action related to performance of a goal may be configured for presentation to the user by a virtual agent. Further, in some embodiments, the content corresponding to the action may be generated based on a progress level of the user with respect to accomplishment of the goal. In some embodiments, generating content may include selecting the content. In some embodiments, the progress level may be determined based on a quantity of the goal that has been accomplished by the user and/or a context score, which may be based on a context surrounding the user, which may be favorable or unfavorable to the user accomplishing the goal.

Moreover, in some embodiments, as will be described later in further detail, the quantity of the goal that has been accomplished by the user and/or the context score may be determined based on one or more of the following types of data associated with the user: sensor data, questionnaire data, and user communication data. Thus, in some embodiments, the content of a conversation may be personalized for the user based on data associated with the user. In some embodiments, the action may be input by a second user. In addition, in some embodiments, the action may be crowd-sourced.

As detailed below, in some embodiments, a conversation tree may guide a conversation between the user and the virtual agent and may be generated based on the progress level and/or a user habit. In some embodiments, the conversation tree may be generated by selecting the conversation tree group from a group of conversation trees. In some embodiments, the conversation tree may be selected based on the conversation tree including the content. In some embodiments, the conversation may be determined using the conversation tree when the user selects one or more responses from a predefined number of statements in the conversation tree.

Moreover, in some embodiments, in response to the progress level of the user being determined, a progress level label may be generated that corresponds to the progress level or a range of progress levels that includes the progress level. In some embodiments, the content may be selected based on the progress level label. In particular, in some embodiments, the content may be selected based on comparison of the progress level label and a content label assigned to the content. In these and other embodiments, the content may be selected based on the content including a content label that matches the progress level label or that corresponds to another progress level below the progress level. The content label of particular content may correspond to a progress level or range of progress levels associated with an action corresponding to the content. For example, the content label of particular content may correspond to a progress level of another user when the other user started or performed the action corresponding to the content.

In addition or as an alternative to selecting the content based on the progress level, in some embodiments, a conversation tree may be selected based on the progress level. In some embodiments, the conversation tree may be selected based on a comparison of the progress level label and a conversation tree label assigned to the conversation tree. In particular, in some embodiments, the conversation tree may be selected based on the conversation tree including a conversation tree label that matches the progress level label or that corresponds to another progress level below the progress level.

In some embodiments, in response to receiving new data reflecting a change in the progress level and/or the progress level label, the conversation may be dynamically updated by selecting new content and/or a new conversation tree, as will be explained later in more detail.

FIG. 1A is a diagram representing an example system 100 configured to determine an accomplishment level 112 and/or a context score 114, arranged in accordance with at least one embodiment described in the present disclosure. In some embodiments, the system 100 may include a conversation module 102 configured to determine the accomplishment level 112 and/or the context score 114. In some embodiments, the goal 104 of a user may be manually input by the user. Additionally or alternatively, in some embodiments, the conversation module 102 may be configured to present one or more possible goals to the user, and the user may select the goal 104 from the possible goals. In some embodiments, the possible goals may be entered by other users and may be crowdsourced. In some embodiments, crowdsourcing the possible goals entered by other users may include polling the other users to determined which of the possible goals entered by the other users are popular among the other users. For example, the other users may vote on the possible goals entered by the other users. In some embodiments, the possible goals may be prebuilt and/or may be derived from various online resources, such as blogs, advice columns, etc.

In some embodiments, the conversation module 102 may be configured to receive the goal 104 and/or progress data related to accomplishment of the goal 104 by the user. Specifically, the progress data may include one or more of the following types of data: sensor data 106, questionnaire data 108, and user communication data 110. In some embodiments, the conversation module 102 may determine, based on the progress data, the accomplishment level 112 and/or the context score 114.

In the present disclosure, the term "sensor" may refer to a physical sensor that may sense or detect one or more indicators or parameters. In the present disclosure, the term "sensor" may also refer to a system, apparatus, device, or module that may acquire information. In some embodiments, the sensors 106 may include one or more of the following: a weather sensor, a location sensor, a schedule sensor, a heart rate sensor, a motion sensor, a sleep sensor, and a time sensor.

The location sensor may include any suitable system, apparatus, device, or module configured to detect or determine a location of the user. For example, the location sensor may include a GPS receiver, a Wi-Fi signal detector, a GSM signal detector, a Bluetooth beacon detector, an Internet Protocol (IP) address detector or any other system, apparatus, device, or module that may detect or determine a location.

The weather sensor may include any suitable system, apparatus, device, or module configured to acquire or measure weather information for the user's location based on the determined location. For example, the weather sensor may be configured to retrieve a weather report from the Internet for the determined location. In these or other embodiments, the weather sensor may include one or more sensors that may detect weather conditions in its surrounding environment. For example, in some embodiments, the weather sensor may include one or more of the following: a temperature sensor, a barometric sensor, a humidity sensor, etc.

The schedule sensor may include any suitable system, apparatus, device, or module configured to extract schedule data from one or more calendars associated with the user. For example, the schedule sensor may be configured to extract schedule data from the user's Outlook Calendar, Google Calendar, or other electronic calendar. The schedule data may be included in progress data in some embodiments.

The heart rate sensor may include any suitable system, apparatus, device, or module configured to measure or determine heart rate or indicators of heart rate. For example, the heart rate sensor may include one or more sensors configured to detect a pulse, a skin temperature, etc. In these or other embodiments, the heart rate sensor may include one or more systems, apparatuses, devices, or modules configured to determine the heart rate based on the detected indicators.

The motion sensor may include any suitable system, apparatus, device, or module configured to determine or detect motion. For example, in some embodiments, the motion sensor may include any suitable system, apparatus, device, or routine capable of detecting or determining one or more of the following: tilt, shake, rotation, swing, and any other motion. In these or other embodiments, the motion sensor may include one or more of the following sensors: a gyroscope, an accelerometer, a magnetometer, a pedometer, a GPS receiver, and any other sensor that may detect motion. Additionally or alternatively, the motion sensor may include one or more systems, apparatuses, devices, or modules configured to determine motion based on the information that may be detected by the sensors.

The sleep sensor may include any suitable system, apparatus, device, or module configured to determine whether the user is sleeping and/or to detect indications that the user is sleeping. In some embodiments, the sleep sensor may include a physical sensor capable of detecting indications of whether the user is sleeping, how much the user has slept, the user's sleep patterns, how well the user has slept or a quality of the user's sleep, etc. In some embodiments, the sensors may be included in or connected to a user device. In some embodiments, the sensors may be wirelessly connected to the user device. In these or other embodiments, the sleep sensor may include one or more systems, apparatuses, devices, or modules configured to determine that the user is sleeping based on the indicators.

The time sensor may include any suitable system, apparatus, device, or module configured to detect or determine a time of day. The time sensor may include, for example, a clock.

In some embodiments, one or more questionnaires may gather the questionnaire data 108 from the user. In some embodiments, a particular questionnaire may relate to accomplishment of the goal of the user. For example, the goal of the user may include consumption by the user of a certain number of grams of protein per day, and the particular questionnaire may include questions such as, for example, "What did you eat for lunch?" or "What did you eat for dinner?" As another example, the goal may include exercising thirty minutes per day, and the particular questionnaire may include questions such as, for example, "Have you spent any time exercising today?" or "Did you walk up the stairs to work?" or "How much free time do you have today to exercise?" The questionnaire data 108 obtained from the questionnaires may relate to any number of topics related to accomplishment of the goal of the user, such as, for example, the user's emotions, motivation, schedule, social interactions, meals, etc. In some embodiments, the conversation module 102 may be configured to present the questionnaires to the user using a user device, such as, for example, a smart phone. In some embodiments, the conversation module 102 may be configured to obtain the questionnaire data 108 from the user via a user interface of the user device that may include an input unit. The user interface may include for example, a keyboard, a stylus, a touch screen, a smart phone, a voice input, voice recognition, a microphone, a mouse, etc.

In some embodiments, the conversation module 102 may analyze user communication data 110. The user communication data 110 may be obtained from one or more communications made by the user. In some embodiments, the communications may include one or more of the following: verbal statements made by the user, written statements made by the user, and body language of the user. The communications may include, for example, text messages, phone calls, video chats, or other communications. In some embodiments, the communications may be made by the user to another person. In some embodiments, the other person may interpret the communications and input the user communication data 110, which may be received by the conversation module 102. In some embodiments, the conversation module 102 may be configured to interpret the communications and/or extrapolate information from the communications to obtain the user communication data 110.

In some embodiments, the conversation module 102 may be configured to determine the accomplishment level 112 based on the progress level. The accomplishment level 112 may indicate a degree of accomplishment of the goal by the user. For example, the accomplishment level 112 may include a quantity of the goal that has or has not been accomplished by the user. For example, the goal of the user may include walking ten thousand (10,000) steps per day, and the sensor data 106 may indicate the user has walked five thousand (5,000) steps on a given day. Based on the sensor data 106, the conversation module 102 may be configured to determine that the accomplishment level 112 is fifty (50) percent by dividing the number of steps walked by the user on the given day (e.g., 5,000) by a target number of steps to walk per day (e.g., 10,000). The accomplishment level 112 may correspond to a percentage or any other value indicating the degree of accomplishment of the goal.

As another example, the goal of the user may include consumption by the user of sixty (60) grams of protein per day, and the questionnaire data 108 may indicate the user has consumed fifteen (15) grams of protein on a given day. Based on the questionnaire data 108, the conversation module 102 may be configured to determined that the accomplishment level 112 is twenty-five (25) percent by dividing the number of grams consumed by the user on the given day (e.g., 15) by a target number of grams to consume per day (e.g., 60). Additionally or alternatively, in some embodiments, the conversation module 102 may be configured to determine an accomplishment level 112 of the goal that has not been accomplished based on the progress data, and the accomplishment level 112 may be used to determine the progress level.

Additionally or alternatively, in some embodiments, the conversation module 102 may be configured to determine, based on the progress data, a context of the user, which may be favorable or unfavorable to the user accomplishing the goal. In some embodiments, the context of the user may be determined from any and/or all progress data that is not related to the accomplishment level 112. In some embodiments, the conversation module 102 may be configured to label the progress data as positive or negative based on whether the progress data indicates a context that is favorable to accomplishment of the goal by the user or a context that is unfavorable to accomplishment of the goal by the user. In some embodiments, the conversation module 102 may be configured to label particular progress data as positive or negative with respect to a particular goal of the user. For example, the user communication data 110 may include the following statement made by the user: "I am feeling my willpower slip away." In some embodiments, another person may interpret the statement "I am feeling my willpower slip away" and input user communication data 110 that may indicate that the context, in this example a mood or energy level, of the user is unfavorable to accomplishment of the goal by the user. The conversation module 102 may be configured to receive and/or determine the accomplishment level 112 and may label the user communication data 110 as negative with respect to accomplishment of the goal.

As another example, particular sensor data 106, received by the conversation module 102 from, for example, a time sensor, may indicate that a time of day is eleven (11) post meridiem (p.m.), leaving only one (1) hour left for the user to accomplish the goal. Based on the sensor data 106, the conversation module 102 may be configured to determine that the context, in this example a time remaining to accomplish the goal, of the user is unfavorable to accomplishment of the goal by the user and label the sensor data 106 as negative with respect to accomplishment of the goal.

As a further example, particular sensor data 106, received by the conversation module 102 from a weather sensor, may indicate that a thunderstorm has occurred or will occur. Based on the particular sensor data 106, the conversation module 102 may be configured to determine that the context, in this example a weather event, surrounding the user is unfavorable with respect to accomplishment of a particular goal of the user of "Bike twenty (20) miles" and may label the sensor data 106 as negative with respect to accomplishment of the particular goal. In some embodiments, correlations between various goals and the sensor data 106 may be pre-defined, and the conversation module 102 may be configured to determine particular sensor data is related to a particular goal based on the pre-defined correlations.

As yet another example, particular sensor data 106, received by the conversation module 102 from a schedule sensor, may indicate that the user's schedule is full with activities unrelated to the goal. Based on the particular sensor data 106, the conversation module 102 may be configured to determine that the context surrounding the user is unfavorable with respect to accomplishment of a particular goal of the user of "Read a book for two (2) hours each day" and may label the sensor data 106 as negative with respect to accomplishment of the particular goal. In some embodiments, the conversation module 102 may be configured to use techniques such as, for example, keyword matching, topic modelling, and/or manual tagging in order to determine based on the user's schedule whether the context surrounding the user is favorable or unfavorable with respect to accomplishment of a particular goal of the user.

In some embodiments, the conversation module 102 may be configured to determine a context score based on the progress data, according to a context function, an example of which is described below in the present disclosure. The context score may correspond to a favorability or unfavorability of a context of the user with respect to accomplishment of the goal by the user. In some embodiments, the context score may be computed using machine learning techniques, such as, for example, singular value decomposition (SVD), clustering, etc. Various context functions may be used to determine the context score. The present disclosure merely describes an example of how the context score may be determined according to a context function.

For example, according to the context function, the context score may be assigned a value, such as, for example, two (2), when a percentage of progress data, labeled as positive with respect to a particular goal of the user, satisfies a threshold percentage with respect to progress data labeled as negative with respect to the particular goal. For example, the threshold percentage may equal fifty (50) percent, and when the positively labeled progress data exceeds fifty (50) percent of total progress data that includes positively labeled progress data and negatively labeled progress data, the context score may be assigned a value of two (2). According to the context function, the context score may be calculated to equal another value, such as, for example, one (1), when the positively labeled progress data does not exceed the threshold percentage, for example, fifty (50) percent of the total progress data.

Figure 1B:
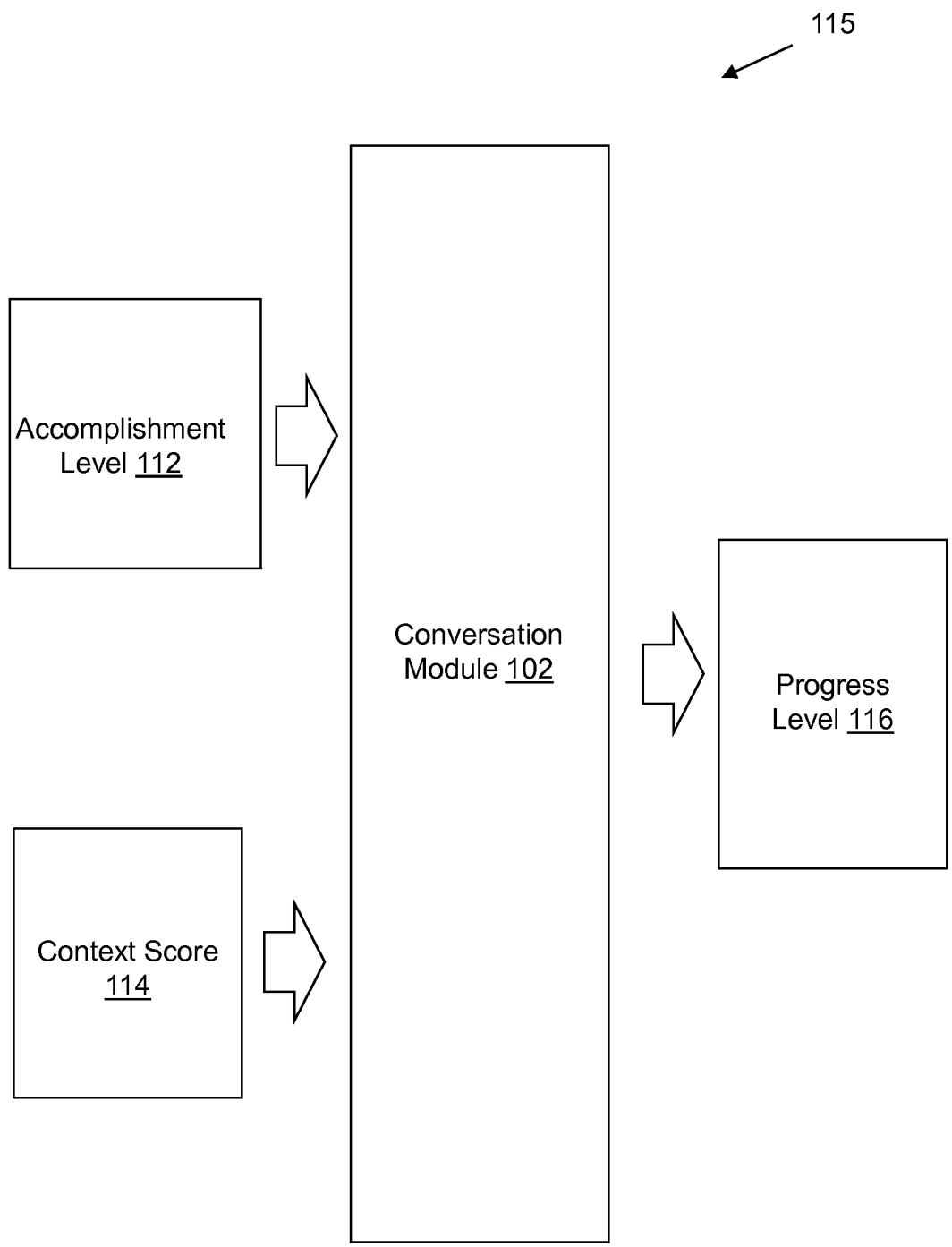
FIG. 1B is a diagram representing another example system configured to determine a progress level of a user.

FIG. 1B is a diagram representing another example system 115 configured to determine a progress level of a user. In some embodiments, the conversation module 102 may be configured to determine, based on the progress data, a progress level 116 of the user. The progress level 116 may correspond to the user's progress with respect to accomplishment of the goal. In some embodiments, the conversation module 102 may be configured to determine the progress level 116 based on the accomplishment level 112 and/or the context score 114. In some embodiments, the conversation module 102 may be configured to determine the progress level 116 according to a progress level function, an example of which is described in the present disclosure. Various progress level functions may be used to determine progress level 116 based on the accomplishment level 112 and/or the context score 114, determined based on the progress data. The present disclosure merely describes an example of how the progress level 116 may be determined according to a progress level function. In some embodiments, the conversation module 102 may be configured to calculate the progress level 116, p, according to the following example expression in some embodiments:

$$p = q \times c$$

In the above expression, q and c may represent the accomplishment level 112 and the context score 114, respectively.

In some embodiments, the conversation module 102 may be configured to generate a progress level label that corresponds to the progress level 116. In some embodiments, the progress level label may be generated based on the progress level 116 meeting or exceeding a threshold value, being below a threshold value, or being between threshold values. For example, in response to the progress level 116 being below a first threshold value, below a second threshold value, below a third threshold value, or below a fourth threshold value, a progress level label of "Failure," "Too little," "Almost there," and "Success" may be generated, respectively. In response to the context score 114 indicating a context surrounding accomplishment of the goal being unfavorable or challenging, a progress level label of "Understandable" may be generated. In some embodiments, in response to the context score 114 being below a particular threshold, the "Understandable" progress level label may be generated regardless of the accomplishment level 112. As referred to in the present disclosure, a threshold value may include a single value or a range of values.

In some embodiments, the conversation module 102 may be configured to determine a progress level based solely on q, or the accomplishment level. In these and other embodiments, each of the progress level labels may have a precise definition based on the progress level. For example, in response to the user achieving between eight-five percent (85%) and one-hundred percent (100%) of the goal of the user, the conversation module 102 may generate a progress level label of "Success." As another example, in response to the user achieving between seventy percent (70%) and ninety percent (90%) of the goal of the user, the conversation module 102 may generate a progress level label of "Almost there." As a further example, in response to the user achieving between ten percent (10%) and eighty percent (80%) of the goal of the user, the conversation module 102 may generate a progress level label of "Too little." As yet another example, in response to the user achieving between zero and twenty-five percent (25%) of the goal of the user, the conversation module 102 may generate a progress level label of "Failure."

Figure 1C:
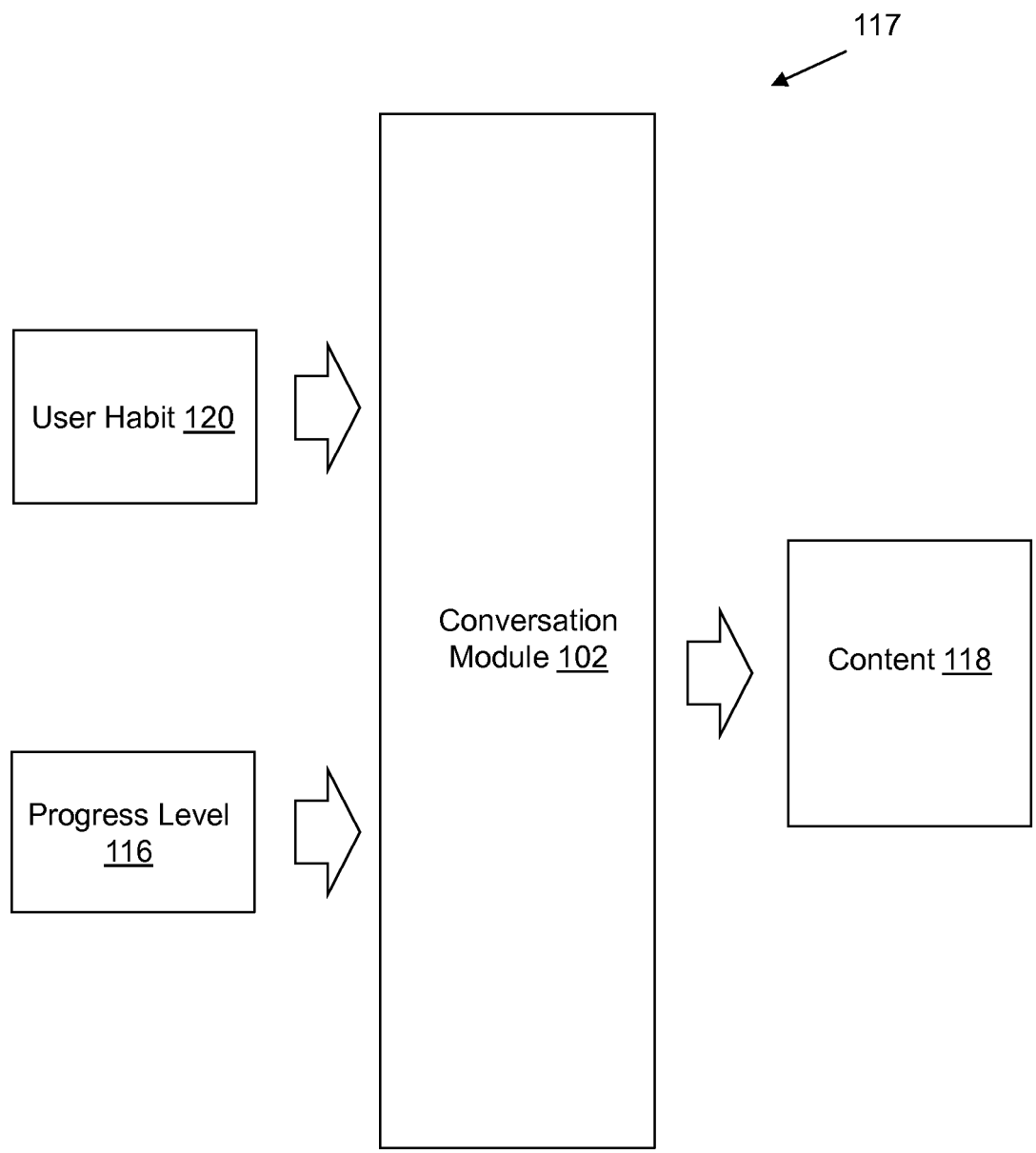
FIG. 1C is a diagram representing another example system configured to select content to include in a conversation between a user and a virtual agent.

FIG. 1C is a diagram representing another example system 117 configured to select content 118 that may be included in a conversation between a user and a virtual agent. In some embodiments, the content 118 may include or correspond to an action related to performance of the goal 104. In some embodiments, the content 118 may include or correspond to an action of another user related to performance of the goal 104. In some embodiments, the action may be input by the other user and received by the conversation module 102. In some embodiments, the action may be generated by the conversation module 102 without input by the other user. For example, the action may be derived from various online resources, such as blogs, advice columns, etc.

In some embodiments, the action may be related to performance of the goal 104 by being related to performance of another goal that is related to the goal 104. For example, the content 118 may include a particular action, such as saving coins in a jar, related to performance of a particular goal 104 of saving money. As another example, the content 118 may include a particular action, such as eating smaller meals throughout the day, related to performance of a particular goal 104 of limiting calorie intake and/or losing weight. As yet another example, the child node 214 of FIG. 2 may include or correspond to the content 118, as will be explained later in more detail. In some embodiments, the conversation module 102 may be configured to select the content 118 based on one or more of the following: a progress level 116 and a user habit 120. For example, in some embodiments, the content 118 may be selected based on the progress level 116 satisfying a threshold value. In some embodiments, the conversation module 102 may be configured to select first content 118 based on the progress level 116 satisfying a threshold value and second content 118 based on the progress level 116 not satisfying the threshold value or satisfying another threshold value.

In particular, in some embodiments, the conversation module 102 may be configured to select content 118 based on a progress level label. For example, the content 118 may be selected based on comparison of the progress level label and a content label assigned to the content 118. In particular, in some embodiments, the conversation module 102 may be configured to select the content 118 in response to the content 118 including a content label that matches the progress level label or corresponds to another progress level below the progress level.

As an example, progress level labels of "Failure," "Too little," "Almost there," and "Success" may correspond to progressively higher progress levels or progress level ranges. Thus, a progress level label of "Failure" or "Too little" may indicate a user is further from accomplishment of the goal than a progress level label of "Almost there" or "Success." In some embodiments, in response to the progress level label and the content label both corresponding to "Failure," "Too little," "Almost there," or "Success," the conversation module 102 may be configured to select the content 118. In some embodiments, in response to the progress level label of "Almost there" and the content label corresponding to another progress level below the progress level, such, as for example, "Almost there" or "Too little," the conversation module 102 may be configured to select the content 118.

As illustrated in FIG. 1C, in some embodiments, the conversation module 102 may be configured to select the content 118 based on a user habit 120. In some embodiments, the conversation module 102 may be configured to determine the user habit 120 based on a pattern of change in the progress level of the user with respect to presentation of a particular type of content 118 to the user by the virtual agent. For example, the conversation module 102 may be configured to determine, based on historical data, a pattern of the progress level increasing in response to presentation of content 118 corresponding to a particular type of action. As a more specific example, where the goal relates generally to exercise, the progress level may habitually increase in response to presentation of content 118 relating to running or stretching. The pattern of the progress level increasing in response to presentation of the content 118 may correspond to the user habit of increasing user activity with respect to accomplishing the goal when the content 118 is presented. The conversation module 102 may be configured to select the content 118 based on the pattern of change and/or the user habit.

As another example, the conversation module 102 may be configured to determine based on historical data a pattern of the progress level increasing in response to presentation of content 118 corresponding to a particular tone. As a more specific example, the progress level may habitually increase in response to presentation of the content 118 in a sympathetic tone as opposed to a fact-based, harsh tone. For example, the user may historically respond better or with increased progress towards the goal when the sympathetic tone is used than when the fact-based, harsh tone is used. The conversation module 102 may be configured to select the content 118 based on the particular tone. In some embodiments, the conversation module may be configured to select the content 118 based on one or more of the following: the pattern of change, the user habit, and the particular tone of the content.

In some embodiments, the conversation module 102 may be configured to select the content 118 based at least in part on the corresponding action being crowdsourced. In some embodiments, one or more particular actions entered by the other users may be crowdsourced. In some embodiments, crowdsourcing the particular actions input by the other users may include polling the other users to determine which of the particular actions entered by the other users are popular among the other users. For example, the other users may vote on the particular actions entered by the other users. The conversation module 102 may be configured to select the content 118 from multiple content 118. The multiple content 118 may be selected, for example, based on each of the multiple content 118 being determined to be more or most popular with respect to accomplishment of one or more of the following: a particular goal 104, a particular accomplishment level 112, and/or a particular progress level 116. The conversation module 102 may be configured to select the content 118 from the multiple content 118 based on to include in the conversation from the multiple content 118 based on, for example, a progress level 116 and/or the user habit 120.

Figure 1D:
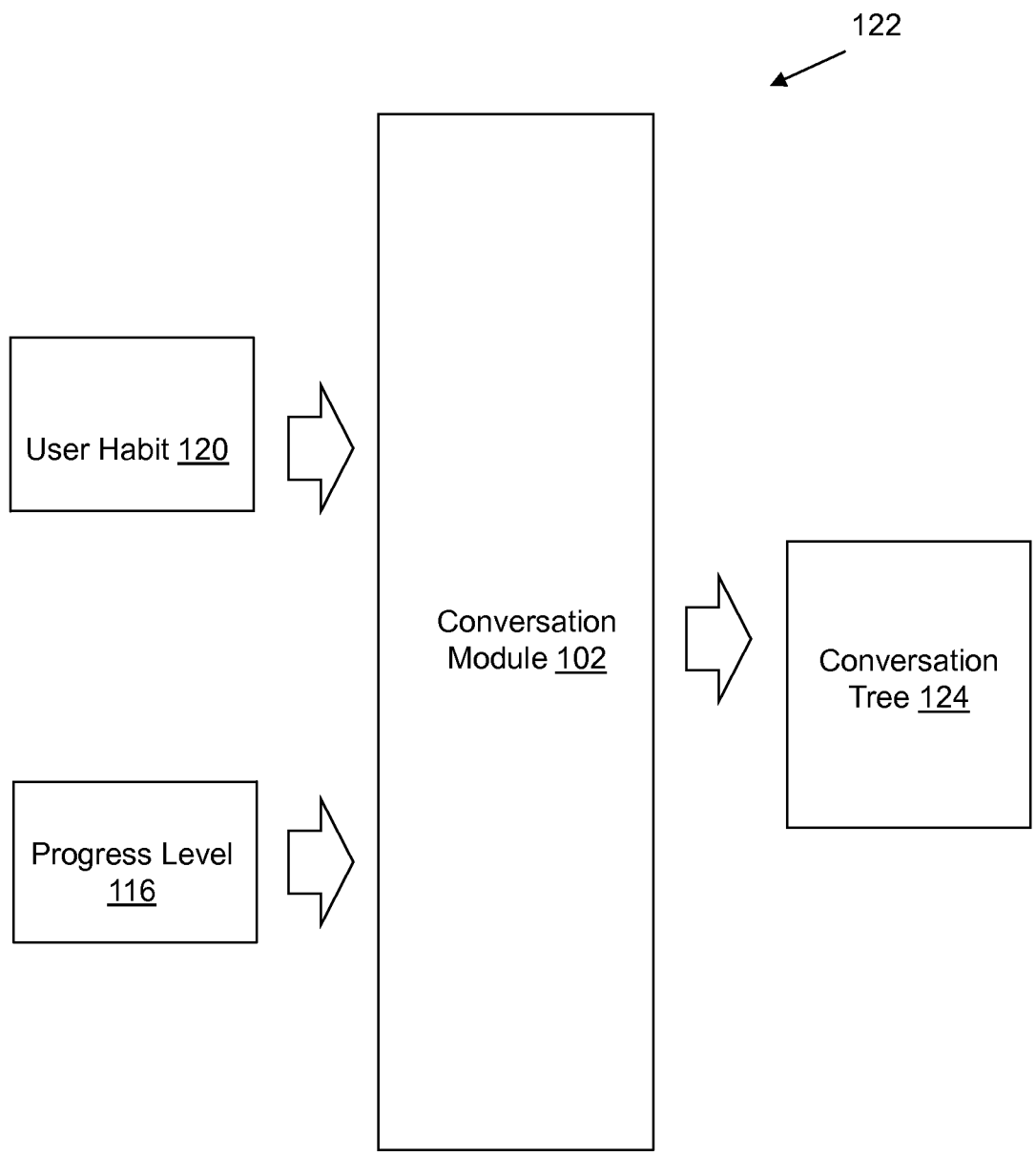
FIG. 1D is a diagram representing another example system configured to select a conversation tree to guide a conversation between a user and a virtual agent.

FIG. 1D is a diagram representing another example system 122 configured to generate a conversation tree 124 to guide a conversation between a user and a virtual agent. In some embodiments, the conversation tree 124 may include a collection of nodes, each node corresponding to a statement of the virtual agent or the user. In some embodiments, the collection of nodes may be arranged in a hierarchical tree structure with a parent node and one or more child nodes. The parent node may include any node that has nodes below it (child nodes). A particular node may be both a parent node and a child node. Each node corresponding to a statement by the virtual agent may have one or more child nodes, each corresponding to a statement by the user. In some embodiments, the parent node may represent a first or opening statement in a conversation between the virtual agent and the user and may correspond to a statement of the virtual agent or the user; either the virtual agent or the user may initiate the conversation.

Figure 2:
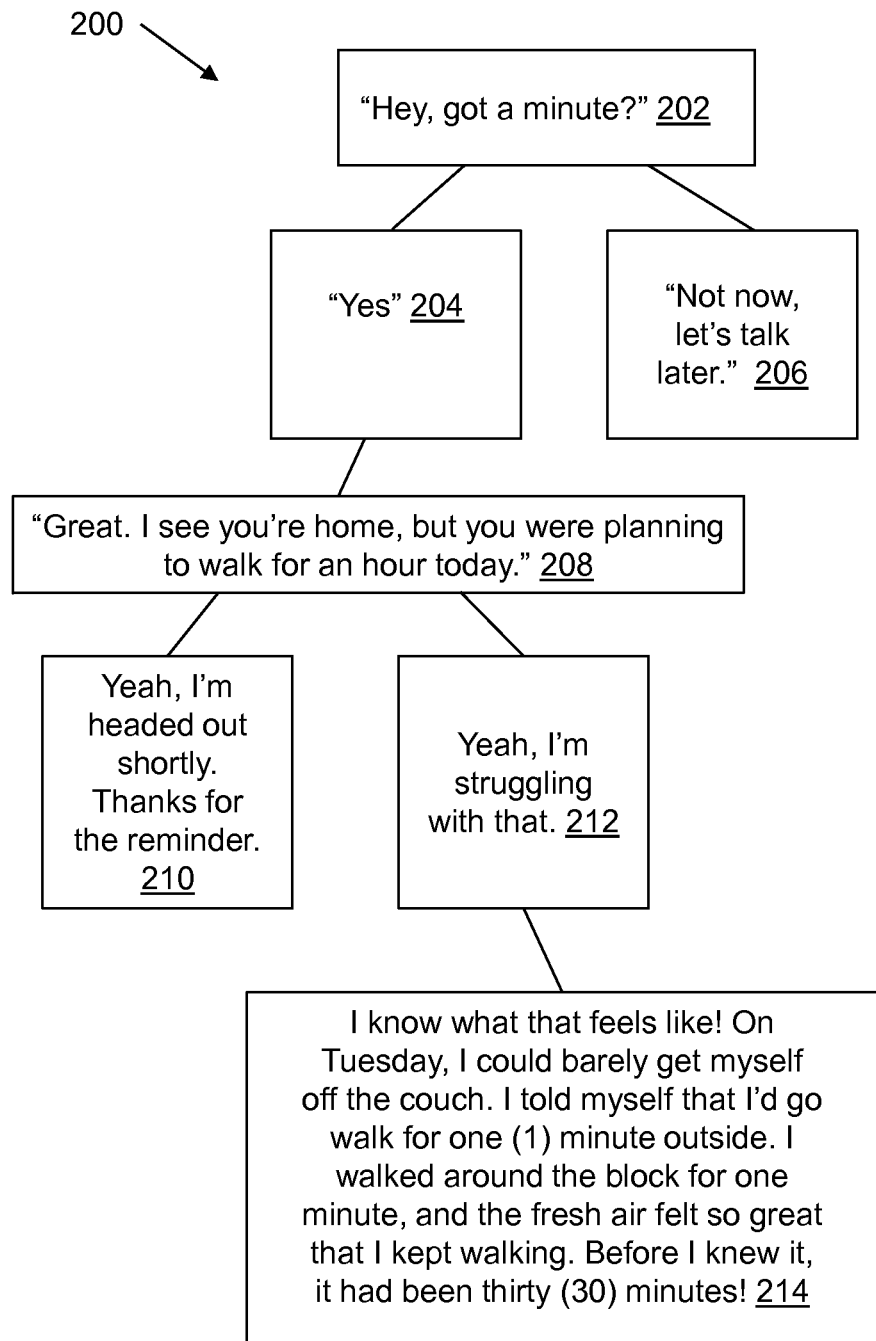
FIG. 2 is a diagram representing an example conversation tree.

For example, referring now to FIG. 2, a parent node 202 may correspond to a statement of the virtual agent, such as, for example, "Hey, got a minute?" The parent node 202 may include child nodes 204 and 206, which may correspond to statements by the user. Child nodes 210 and 212 may also correspond to statements by the user. Child node 214 may include or correspond to the content 118 of FIG. 1. Child nodes 208 and 214 may also correspond to statements by the virtual agent. In some embodiments, the child nodes 204, 206, 210, and 212 may correspond to statements that may be selected by the user, using for example, the user device. Additionally or alternatively, in some embodiments, the statements may be selected by the user and/or manually input by the user using, for example, a user interface of a user device. Additionally or alternatively, in some embodiments, the statements of the user may be spoken by the user. In some embodiments, the statements by the user and/or the statements by the virtual agent may be selected from a group of static statements, one or more of which may be crowdsourced or voted on by other users.

Returning to FIG. 1D, in some embodiments, the conversation module 102 may be configured to select the conversation tree 124 based on the conversation tree including the content 118, which may be selected based on the progress level 116 and/or the user habit 120. Additionally or alternatively, in some embodiments, the conversation module 102 may be configured to select the conversation tree 124 based on one or more of the following: a progress level 116 and a user habit 120. For example, similar to the content 118, in some embodiments, the conversation tree 124 may be selected based on the progress level 116 satisfying a threshold value. In some embodiments, the conversation module 102 may be configured to select a first conversation tree 124 based on the progress level 116 satisfying a threshold value and to select a second conversation tree 124 based on the progress level 116 not satisfying the threshold value or satisfying another threshold value.

In particular, in some embodiments, the conversation module 102 may be configured to select the conversation tree 124 based on a progress level label. For example, the conversation tree 124 may be selected based on comparison of the progress level label and a conversation tree label assigned to the conversation tree 124. In particular, in some embodiments, the conversation module 102 may be configured to select the conversation tree 124 based on the conversation tree 124 including a conversation tree label that matches the progress level label or corresponds to another progress level below the progress level.

As an example, progress level labels of "Failure," "Too little," "Almost there," and "Success" may correspond to progressively higher progress levels or progress level ranges. Thus, a progress level label of "Failure" or "Too little" may indicate a user is further from accomplishment of the goal than a progress level label of "Almost there" or "Success." In some embodiments, in response to the progress level label and the conversation tree label both corresponding to "Failure," "Too little," "Almost there," or "Success," the conversation module 102 may be configured to select the conversation tree 124. In some embodiments, in response to the progress level label corresponding to "Almost there" and the conversation tree label corresponding to another progress level below the progress level, such, as for example, "Almost there" or "Too little," the conversation module 102 may be configured to select the conversation tree 124. The conversation tree illustrated in FIG. 2, for example, may correspond to a "Too little" conversation tree 124.

As illustrated in FIG. 1D, in some embodiments, the conversation module 102 may be configured to select the conversation tree 124 based on a user habit 120, similar to selection of the content 118 in FIG. 1C. In some embodiments, the conversation module 102 may be configured to determine the user habit 120 based on a pattern of change in the progress level of the user with respect to presentation of a particular type of conversation tree 124 to the user by the virtual agent. For example, the conversation module 102 may be configured to determine based, on historical data, a pattern of the progress level increasing in response to presentation of a conversation tree 124 that includes a particular type of content 118. As a more specific example, where the goal relates generally to exercise, the progress level may habitually increase in response to presentation of a conversation tree 124 including content 118 relating to running or stretching. The pattern of the progress level increasing in response to presentation of the conversation tree 124 may correspond to the user habit of increasing user activity with respect to accomplishing the goal when the conversation tree 124 is presented. In some embodiments, the conversation module 102 may be configured to select the conversation tree 124 based on the pattern of change and/or the user habit.

As another example, the conversation module 102 may be configured to determine based on historical data a pattern of the progress level increasing in response to presentation of a conversation tree 124 corresponding to a particular tone. As a more specific example, the progress level may habitually increase in response to presentation of a conversation tree 124 in which the virtual agent uses a sympathetic tone. The conversation module 102 may be configured to select the conversation tree 124 based on the particular tone. In some embodiments, the conversation module may be configured to select the conversation tree 124 based on one or more of the following: the pattern of change, the user habit, and the particular tone of the content.

In some embodiments, the content 118 and/or the conversation tree 124 may be configured for presentation to the user by a virtual agent and/or human. In some embodiments, the virtual agent may be programmed to converse with the user using one or more of the following: text, visual, and audio data, which may be configured to be presented to the user. In some embodiments, the data may be configured to be presented to the user in a vehicle, such as, for example, a car. In some embodiments, the data may be configured to be presented to the user using a robot or another computing device, such as, for example, a tablet, notebook, smartphone, or other computing devices. In some embodiments, the virtual agent may converse with the user and/or deliver the content 118 to the user using a machine-synthesized speech. In some embodiments, a voice of the virtual agent may be obtained from an interactive voice response (IVR) voice, pre-programmed human voices, and/or any other synthetic voices. In some embodiments, the user may respond to the virtual agent by one or more of the following: selecting a response, manually inputting a response, and providing verbal input. In some embodiments, the response may be selected and/or manually input using the keypad of the user device.

Figure 3:
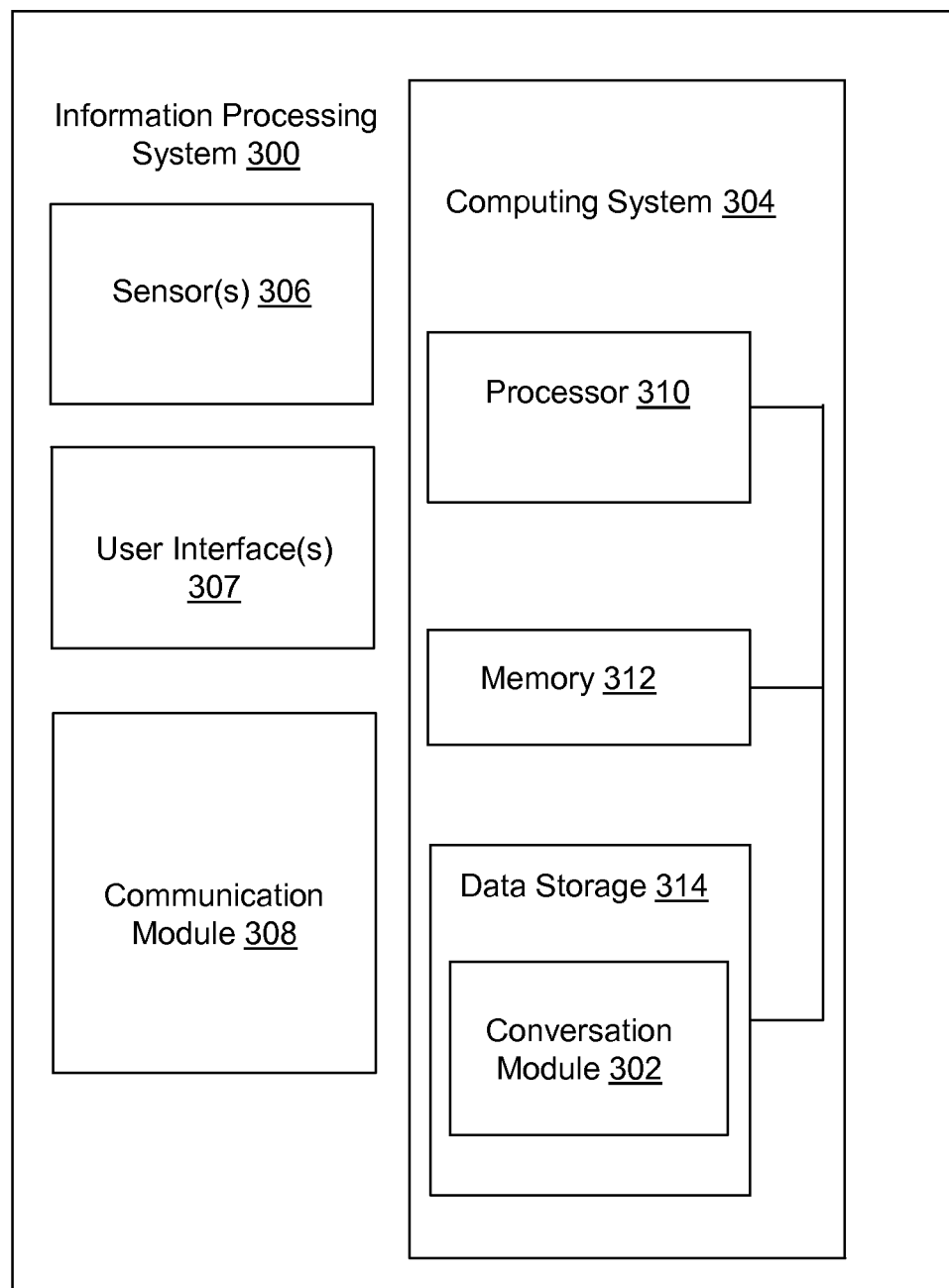
FIG. 3 is a block diagram illustrating an example information processing system that may include a conversation module.

FIG. 3 is a block diagram illustrating an example information processing system 300 that may include a conversation module 302, arranged according to at least one embodiment described in the present disclosure. The conversation module 302 may include or correspond to the conversation module 102 of FIGS. 1A-1D. The information processing system 300 may include a computing system 304, one or more sensors 306, a user interface 307, and a communication module 308. The sensors 306 may include one or more of the following: a weather sensor, a location sensor, a schedule sensor, a heart rate sensor, a motion sensor, a sleep sensor, and a time sensor, such as described above. The user interface 307 may include one or more of the following a keyboard, a stylus, a touch screen, a smart phone, a voice input, voice recognition, a microphone, a mouse, etc.

The computing system 304 may include any suitable system, apparatus, or device configured to generate a conversation between the user and the virtual agent using the conversation module 302. The computing system 304 may include a processor 310 communicatively coupled to a memory 212. In some embodiments, the conversation module 302 may be embodied in logic or instructions resident in the data storage 314 for execution by the processor 310. Additionally or alternatively, one or more modules of one or more of the sensors 306 may be embodied in logic or instructions resident in the data storage 314 for execution by the processor 310. Additionally or alternatively, one or more modules of one or more user interfaces 307 may be embodied in logic or instructions resident in the data storage 314 for execution by the processor 310.

The processor 310 may include any suitable special-purpose or general-purpose computer, computing entity, or processing device including various computer hardware or software modules and may be configured to execute instructions stored on any applicable computer-readable storage media. For example, the processor 310 may include a microprocessor, a microcontroller, a digital signal processor (DSP), an application-specific integrated circuit (ASIC), a Field-Programmable Gate Array (FPGA), or any other digital or analog circuitry configured to interpret and/or to execute program instructions and/or to process data. Although illustrated as a single processor in FIG. 3, it is understood that the processor 310 may include any number of processors configured to perform individually or collectively any number of operations described herein. Additionally, one or more of the processors may be present on one or more different electronic devices. In some embodiments, the processor 310 may interpret and/or execute program instructions and/or process data stored in the data storage 314.

The memory 312 may include computer-readable storage media for carrying or having computer-executable instructions or data structures stored thereon. Such computer-readable storage media may be any available media that may be accessed by a general-purpose or special-purpose computer, such as the processor 310. By way of example, and not limitation, such computer-readable storage media may include tangible or non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store desired program code in the form of computer-executable instructions or data structures and which may be accessed by a general-purpose or special-purpose computer. Combinations of the above may also be included within the scope of computer-readable storage media. Computer-executable instructions may include, for example, instructions and data configured to cause the processor 310 to execute instructions that may cause the computing system 304 perform a certain function or group of functions.

The conversation module 302 may include instructions and data configured to cause the processor 310 to execute instructions that may cause the computing system 304 to generate a conversation between the user and the virtual agent. In some embodiments, the computing system 304 may incorporate the conversation module 302 in the data storage 314 as illustrated in FIG. 3. In the present disclosure, reference to "performance" of operations by a conversation module (e.g., the conversation module 102 or 302) may include performance of operations by a corresponding processor or computing system according to instructions or logic stored as the conversation module.

The conversation module 302 may include software including routines for handling communications between the conversation module 302 and other components of the information processing system 300. Additionally or alternatively, the conversation module 302 may be configured to send and receive data, including opportunity data, to and from one or more other entities via a network. In some embodiments, the conversation module 302 may receive progress data from the sensors 306 and/or questionnaires answered by the user and store the progress data in the data storage 314. In these or other embodiments, the communication module 208 may be configured to retrieve data, including progress data, from the data storage 314 and to send the data to the conversation module 302.

Figure 4:
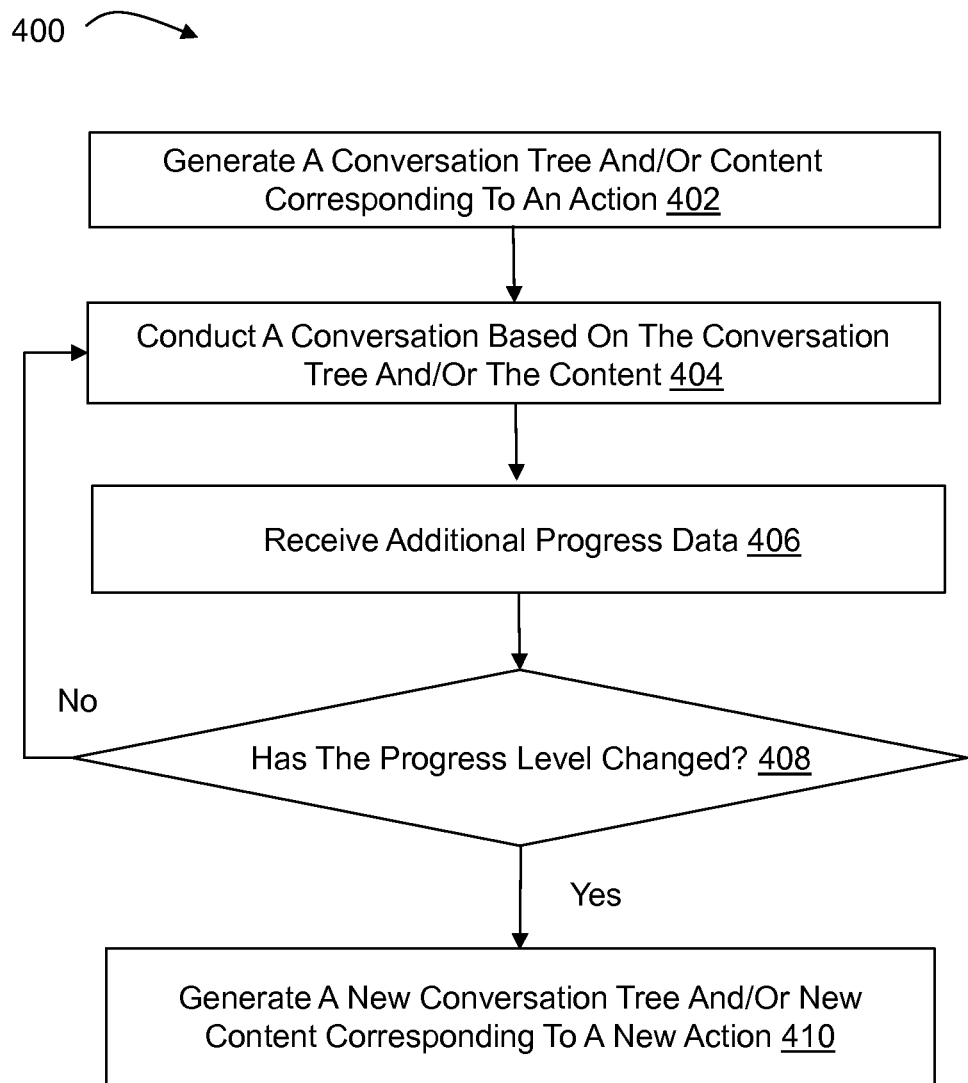
FIG. 4 is a flowchart of an example method of generating a new conversation tree and/or new content corresponding to a story that includes an action.

FIG. 4 is a flowchart of an example method 400 of generating a new conversation tree and/or new content corresponding to an action, arranged in accordance with at least one embodiment described in the present disclosure. One or more operations of the method 400 may be implemented, in whole or in part and individually or collectively, by the conversation module 102 of FIG. 1, the computing system 304 of FIG. 3, or another suitable device, server, and/or system. For example, in some embodiments, some or all of the method 400 may be performed by the conversation module 302 of FIG. 3 being executed on a suitable device, server, and/or system. As illustrated in FIG. 4, a conversation may be dynamically updated based on receipt of new or additional progress data.

At block 402, a conversation tree and/or content corresponding to an action may be generated. The conversation tree may include or correspond to the conversation tree 200 of FIG. 2. The content may include or correspond to the content 118 of FIG. 1. The conversation tree and/or the content may be generated based one or more of the following: a progress level of the user with respect to accomplishment of the goal, a progress level label, and a user habit. The progress level and/or the user habit may include or correspond to the progress level 116 and/or user habit 120 of FIG. 1, respectively. Block 402 may be followed by block 404.

At block 404, a conversation may be conducted based on the conversation tree and/or the content. Block 404 may be followed by block 406.

At block 406, additional progress data may be received. The additional progress data may include one or more of the following: sensor data, questionnaire data, and user communication data. Block 404 may be followed by block 406.

At block 406, it may be determined whether the progress level has changed based on the additional progress data, which may be used to determine a new quantity of a goal of the user that has been accomplished and/or a new context score. Block 408 may be followed by block 410 ("Yes" at block 408) or by block 404 ("No" at block 408).

At block 410, a new conversation tree and/or new content, the new content corresponding to a new action, may be generated based on a new progress level and/or progress level label.

Modifications, additions, or omissions may be made to the method 400 without departing from the scope of the present disclosure. For example, the functions performed in the method 400 may be implemented in differing order. Furthermore, the outlined acts and operations are only provided as examples, and some of the acts and operations may be optional, combined into fewer acts and operations, or expanded into additional acts and operations without detracting from the essence of the disclosed embodiments.

Figure 5:
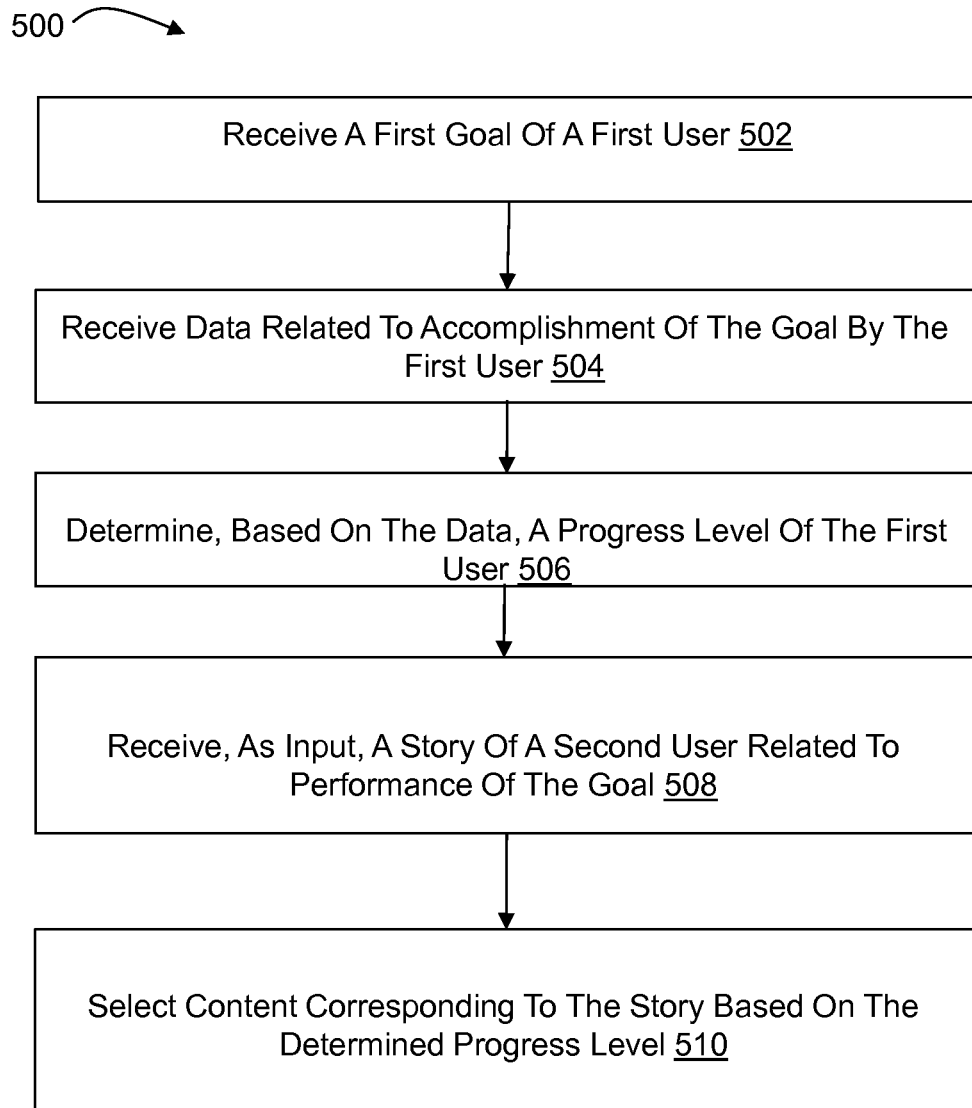
FIG. 5 is a flowchart of an example method of generating a conversation for behavior encouragement.

FIG. 5 is a flowchart of an example method 500 of generating a conversation for behavior encouragement, arranged in accordance with at least one embodiment described in the present disclosure. One or more operations of the method 500 may be implemented, in whole or in part and individually or collectively, by the conversation module 102 of FIG. 1, the computing system 304 of FIG. 3, or another suitable device, server, and/or system. For example, in some embodiments, some or all of the method 500 may be performed by the conversation module 302 of FIG. 3 being executed on a suitable device, server, and/or system.

The method 500 may begin at block 502, where a first goal of a first user may be received. Block 502 may be followed by block 504.

At block 504, data related to accomplishment of the goal by the first user may be received. The data may include progress data. Block 504 may be followed by block 506.

At block 506, a progress level of the first user may be determined based on the data. Block 506 may be followed by block 508.

At block 508, an action of a second user related to performance of the goal may be received as input. Block 508 may be followed by block 510.

At block 510, content corresponding to the action may be selected based on the determined progress level.

Modifications, additions, or omissions may be made to the method 500 without departing from the scope of the present disclosure. For example, the functions performed in the method 500 may be implemented in differing order. Furthermore, the outlined acts and operations are only provided as examples, and some of the acts and operations may be optional, combined into fewer acts and operations, or expanded into additional acts and operations without detracting from the essence of the disclosed embodiments.

For example, the content may be selected based on the progress level not satisfying a threshold or satisfying the threshold. As another example, the method 500 may include generating a label corresponding to the progress level. The content may include another label, the other label corresponding to the progress level or another progress level below the progress level.

As another example, the method 500 may include one or more of the following: determining, based on the data, an accomplishment level that indicates a degree of accomplishment of the goal by the user, determining, based on the data, a context favorability or unfavorability of a context of the first user with respect to accomplishment of the goal by the first user; and determining the progress level based on the accomplishment level and/or the favorability or unfavorability of the context of the first user with respect to accomplishment of the goal by the first user.

Moreover, the method 500 may include selecting a conversation tree to guide a conversation between the first user and the virtual agent. In some embodiments, the conversation tree may include a plurality of nodes. The plurality of nodes may include a node corresponding to the content. In some embodiments, the conversation tree may be selected based on the progress level not satisfying a threshold. In some embodiments, the conversation tree may be selected based on the progress level satisfying a threshold.

Also, the method 500 may include determining the conversation between the first user and the virtual agent based on selection by the first user of a statement from a predefined number of statements in the conversation tree.

Additionally, the method 500 may include determining a pattern of change in the progress level of the first user with respect to presentation of the content to the first user by the virtual agent. The conversation tree may be selected based on the pattern of change.

As a further example, the method 500 may include receiving additional data that indicates another progress level of the first user with respect to accomplishment of the first goal. In response to receiving the additional data, the method 500 may include updating the progress level of the first user to the other progress level and/or transmitting to the mobile computing device new content related to a new action to accomplish the goal. The new content may be configured for presentation to the first user by the virtual agent.

Figure 6:
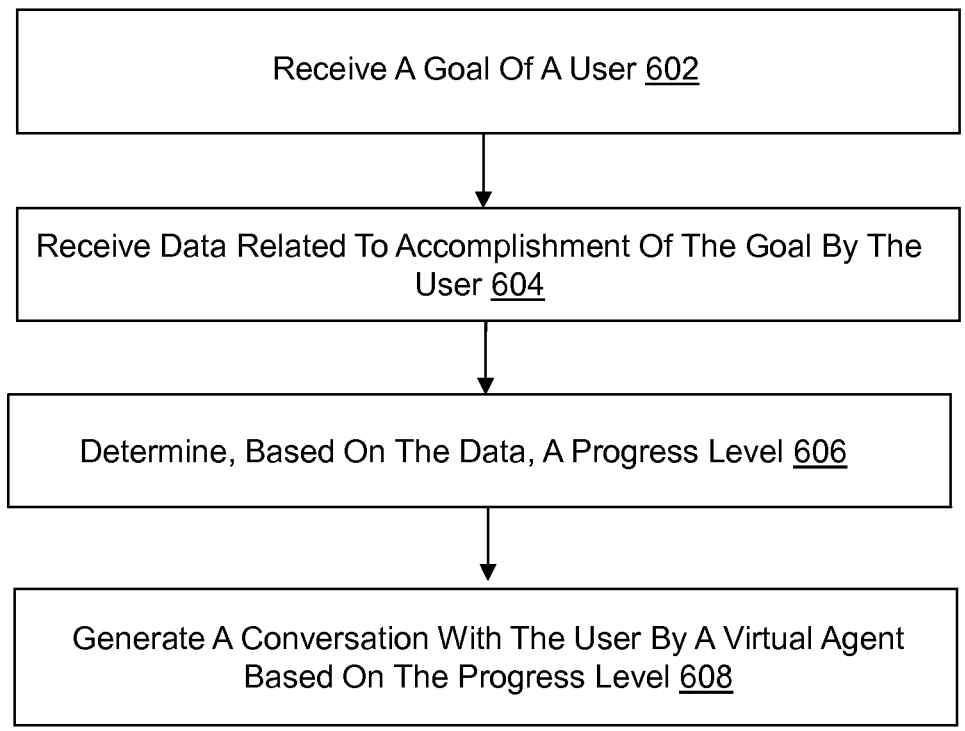
FIG. 6 is a flowchart of another example method of generating a conversation for behavior encouragement.

FIG. 6 is a flowchart of another example method 600 of generating a conversation for behavior encouragement, arranged in accordance with at least one embodiment described in the present disclosure. One or more operations of the method 600 may be implemented, in whole or in part and individually or collectively, by the conversation module 102 of FIG. 1, the computing system 304 of FIG. 3, or another suitable device, server, and/or system. For example, in some embodiments, some or all of the method 600 may be performed by the conversation module 302 of FIG. 3 being executed on a suitable device, server, and/or system.

The method 600 may begin at block 602, where a goal of a user may be received. Block 602 may be followed by block 604.

At block 604, data related to accomplishment of the goal by the user may be received. The data may include progress data. Block 604 may be followed by block 606.

At block 606, a progress level may be determined based on the data. Block 606 may be followed by block 608.

At block 608, a conversation between the user and a virtual agent may be generated based on the progress level.

Modifications, additions, or omissions may be made to the method 600 without departing from the scope of the present disclosure. For example, the functions performed in the method 600 may be implemented in differing order. Furthermore, the outlined acts and operations are only provided as examples, and some of the acts and operations may be optional, combined into fewer acts and operations, or expanded into additional acts and operations without detracting from the essence of the disclosed embodiments. For example, the method 600 may include generating a label corresponding to the progress level. In some embodiments, the conversation tree may include another label, the other label corresponding to the progress level or another progress level below the progress level.

As another example, the method 600 may further include receiving, as input, an action of another user related to performance of the goal, and selecting content corresponding to the action based on the determined progress level. In some embodiments, the content may be configured for presentation to the user by a virtual agent. One skilled in the art will appreciate that, for this and other processes and methods disclosed herein, the functions performed in the processes and methods may be implemented in differing order. Furthermore, the outlined acts and operations are only provided as examples, and some of the acts and operations may be optional, combined into fewer acts and operations, or expanded into additional acts and operations without detracting from the essence of the disclosed embodiments.

As indicated above, the embodiments described in the present disclosure may include the use of a special purpose or general purpose computer including various computer hardware or software modules, as discussed in greater detail below. Further, as indicated above, embodiments described in the present disclosure may be implemented using computer-readable media for carrying or having computer-executable instructions or data structures stored thereon.

As used in the present disclosure, the terms "module" or "component" may refer to specific hardware embodiments configured to perform the actions of the module or component and/or software objects or software routines that may be stored on and/or executed by general purpose hardware (e.g., computer-readable media, processing devices, etc.) of the computing system. In some embodiments, the different components, modules, engines, and services described in the present disclosure may be implemented as objects or processes that execute on the computing system (e.g., as separate threads). While some of the system and methods described in the present disclosure are generally described as being implemented in software (stored on and/or executed by general purpose hardware), specific hardware embodiments or a combination of software and specific hardware embodiments are also possible and contemplated. In this description, a "computing entity" may be any computing system as previously defined in the present disclosure, or any module or combination of modulates running on a computing system.

Terms used in the present disclosure and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc.

Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B."

All examples and conditional language recited in the present disclosure are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, various changes, substitutions, and alterations could be made hereto without departing from the spirit and scope of the present disclosure.

What is claimed is:

1. A method comprising:
   receiving a goal of a first user from a mobile computing device of the first user;
   obtaining progress data related to accomplishment of the goal by the first user from one or more of the following: a user interface of the mobile computing device of the first user and a sensor;
   determining, based on the progress data, a progress level of the first user, wherein the progress level corresponds to progress of the first user with respect to accomplishment of the goal;
   identifying an action related to performance of the goal through crowdsourcing online content of other users with respect to accomplishment of the goal;
   determining from the crowdsourcing a popularity indication of the action with respect to the determined progress level;
   determining a first pattern of change of the progress level in response to first content of a first type being presented to the first user, the first content being related to encouraging accomplishment of the goal;
   determining a second pattern of change of the progress level in response to second content of a second type being presented to the first user, the second content being related to encouraging accomplishment of the goal;
   determining that the first content of the first type is more effective than the second content of the second type based on the first pattern of change indicating a greater increase in the progress level than the second pattern of change;
   selecting additional content that includes the action based on the popularity indication of the action with respect to the determined progress, wherein the additional content is selected based on the additional content being of the first type and not the second type in response to determining that the first content of the first type is more effective than the second content of the second type and wherein the additional content is configured for presentation to the first user by a virtual agent; and
   causing the additional content to be presented by the virtual agent on the mobile computing device of the first user.

2. The method of claim 1, wherein the additional content is selected based on the progress level not satisfying a threshold.

3. The method of claim 1, wherein the additional content is selected based on the progress level satisfying a threshold.

4. The method of claim 1, further comprising generating a label corresponding to the progress level,
   wherein the additional content includes another label, wherein the other label corresponds to the progress level or another progress level below the progress level.

5. The method of claim 1, further comprising:
   determining, based on the progress data, an accomplishment level that indicates a degree of accomplishment of the goal by the first user;
   determining, based on the progress data, a context of the first user with respect to accomplishment of the goal by the first user; and
   determining the progress level based on the accomplishment level and the context of the first user with respect to accomplishment of the goal by the first user.

6. The method of claim 1, further comprising selecting a conversation tree to guide a conversation between the first user and the virtual agent, wherein the conversation tree includes a plurality of nodes, wherein the plurality of nodes includes a node corresponding to the additional content.

7. The method of claim 6, wherein the conversation tree is selected based on the progress level not satisfying a threshold.

8. The method of claim 6, wherein the conversation tree is selected based on the progress level satisfying a threshold.

9. The method of claim 6, further comprising determining the conversation between the first user and the virtual agent based on selection by the first user of a statement from a predefined number of statements in the conversation tree.

10. The method of claim 6,
    wherein the conversation tree is selected based on the first pattern of change.

11. The method of claim 1, further comprising:
    obtaining additional progress data that indicates another progress level of the first user with respect to accomplishment of the goal from one or more of the following: the sensor and the user interface of the mobile computing device; and
    in response to receiving the additional progress data:
        updating the progress level of the first user to the other progress level; and
        transmitting, to the mobile computing device, new content related to accomplishing the goal, wherein the new content is configured for presentation to the first user by the virtual agent.

12. The method of claim 1, wherein the progress data is obtained from the user interface in response to input of an answer to a questionnaire by the first user via the user interface.

* * * * *